United States Patent
Zhang et al.

(10) Patent No.: US 12,194,013 B2
(45) Date of Patent: Jan. 14, 2025

(54) APPLICATION OF CHLOROGENIC ACID AND COMPOSITIONS THEREOF IN PREPARATION OF DRUGS FOR TREATING SQUAMOUS CELL CARCINOMA

(71) Applicant: SICHUAN JIUZHANG BIOLOGICAL SCIENCE AND TECHNOLOGY CO., LTD., Sichuan (CN)

(72) Inventors: Jie Zhang, Sichuan (CN); Xiaoguang Chen, Sichuan (CN); Wang Huang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 1051 days.

(21) Appl. No.: 17/054,757

(22) PCT Filed: May 10, 2019

(86) PCT No.: PCT/CN2019/086441
§ 371 (c)(1),
(2) Date: Jul. 30, 2021

(87) PCT Pub. No.: WO2019/214723
PCT Pub. Date: Nov. 14, 2019

(65) Prior Publication Data
US 2021/0353580 A1    Nov. 18, 2021

(30) Foreign Application Priority Data
May 11, 2018 (CN) .......................... 201810449331.1

(51) Int. Cl.
*A61K 31/216* (2006.01)
*A61P 35/00* (2006.01)

(52) U.S. Cl.
CPC ............ *A61K 31/216* (2013.01); *A61P 35/00* (2018.01)

(58) Field of Classification Search
CPC .... A61K 31/216; A61K 31/21; A61K 31/215; A61P 35/00
See application file for complete search history.

(56) References Cited

U.S. PATENT DOCUMENTS

| | | | |
|---|---|---|---|
| 2003/0229140 A1* | 12/2003 | Bandyopadhyay | A61K 31/366 514/533 |
| 2009/0076131 A1 | 3/2009 | Ricciardiello et al. | |
| 2017/0334828 A1* | 11/2017 | Zhang | C07C 67/52 |
| 2021/0085630 A1* | 3/2021 | Zhang | A61K 31/655 |
| 2021/0330626 A1* | 10/2021 | Zhang | A61K 31/506 |
| 2021/0338622 A1* | 11/2021 | Zhang | A61P 35/00 |

FOREIGN PATENT DOCUMENTS

| CN | 108159038 A | 6/2018 |
|---|---|---|
| CN | 108685892 A | 10/2018 |

OTHER PUBLICATIONS

Ito, H.; et al. "Polyphenols from Eriobotrya japonica and their cytotoxicity against human oral tumor cell lines" 2000 Chem. Pharm. Bull., vol. 48, pp. 687-693. (Year: 2000).*
Ortiz, A. L. G.; et al. "Synthesis of p-coumaroylquinic acids and analysis of their interconversion" 2017, Tetrahedron Asymmetry, vol. 28, pp. 419-427. (Year: 2017).*
Kern, M.; et al. "Inhibitors of the epidermal growth factor receptor in apple juice extract" 2005, Mol. Nutr. Food Res., vol. 49, pp. 317-328. (Year: 2005).*
Tanaka, T.; et al. "Inhibition of 4-nitroquinoline-1-oxide-induced rat tongue carcinogenesis by the naturally occurring plant phenolics caffeic, ellagic, chlorogenic and ferulic acids" 1993, Carcinogenesis, vol. 14, pp. 1321-1325. (Year: 1993).*
Rodust, P. M.; et al. "UV-induced squamous cell carcinoma—a role for antiapoptotic signalling pathways" 2009, British Journal of Dermatology, vol. 161, pp. 107-115. (Year: 2009).*
Shahjahani, M.; et al. "Molecular basis of chronic lymphocytic leukemia diagnosis and prognosis" 2015, Cellular Oncology, vol. 38, pp. 93-109. (Year: 2015).*
Jiang, Y. et al.; "Induction of Cytotoxicity by Chlorogenic Acid in Human Oral Tumor Cell Lines," Phytomedicine, vol. 7, No.(6), pp. 483-491, Dec. 31, 2000.

* cited by examiner

*Primary Examiner* — Eric Olson
*Assistant Examiner* — Benjamin M Brandsen
(74) *Attorney, Agent, or Firm* — NKL Law; Allen Xue

(57) ABSTRACT

Chlorogenic acid and/or coumaroylquinic acid are employed in preparation of drugs for treating squamous cell carcinoma. Chlorogenic acid or coumaroylquinic acid can effectively treat squamous cell carcinoma. A combination of chlorogenic acid and coumaroylquinic acid can also achieve effective treatment, can yield a synergistic effect, and has excellent application prospect.

6 Claims, 4 Drawing Sheets

APPLICATION OF CHLOROGENIC ACID AND COMPOSITIONS THEREOF IN PREPARATION OF DRUGS FOR TREATING SQUAMOUS CELL CARCINOMA

TECHNICAL FIELD

The present invention particularly relates to the use of chlorogenic acid in the preparation of drugs for treatment of squamous cell carcinoma. The present invention also relates to the use of the composition containing chlorogenic acid in the preparation of drugs for treatment of squamous cell carcinoma.

BACKGROUND ART

Squamous cell carcinoma (SCC), abbreviated as squamous cancer, is a malignant tumor originated from epidermal keratinocytes or skin accessory structures. It is one of the most common skin malignant tumors in clinic, accounting for 20% of all skin malignant tumors. According to the different location of the disease, it can be divided into head and neck squamous cell carcinoma, skin squamous cell carcinoma, oral squamous cell carcinoma, esophageal squamous cell carcinoma, cervical squamous cell carcinoma, and vaginal squamous cell carcinoma. Although the mortality is not high, the cost of treatment is high. The ratio of SCC incidence rate of male to female in China is 1.5:1.0-2.2:1.0, the age of onset is 50-60 years old, and most of them are found in the exposed parts of head, neck, hands and forearm extension, etc. The population included white people, outdoor workers (farmers, workers, etc.), people exposed to human papillomavirus (HPV) 16, 18 and 31, people with hereditary skin diseases, people with chronic ulcer of skin scar tissue, and so on. Long-term ultraviolet radiation is the most risk factor. The metastasis rate of SCC is 2%-5%. The risk factors that affect metastasis include immunosuppression, tumor diameter >10 ram or invasion depth >6 mm, medium and poor differential type, nerve infiltration, lymphatic vessel infiltration, incomplete resection in the first operation and local recurrence, etc.

The gold standard for treatment of skin SCC is complete surgical resection. Radiation therapy can be used as an auxiliary treatment for surgery or used alone to patients who are not suitable for surgery. The indication depends on the patient's own condition and the characteristics of the tumor. Photodynamic therapy (PDT) is a minimally invasive, non-scarring therapy with selective cytotoxicity, whose action elements are composed of three basic components: photosensitizer, light source, and oxygen. Clinical methods that can also be used include laser therapy, electrochemical therapy, epidermal growth factor receptor (EGFR) inhibitors, gene therapy, sonodynamic therapy, etc. In recent years, as the incidence of SCC is rising, as well as patients' requirements for postoperative quality of life are gradually increasing, how to choose a suitable treatment plan to maximize the preservation or restoration of the appearance and the function in the lesion site, and reduce the possibility of recurrence and metastasis, brings great challenges to medical staff.

Therefore, a new drug that can treat SCC is urgently needed, and no report on the use of chlorogenic acid and coumaroylquinic acid in the treatment of SCC has been found.

CONTENT OF THE INVENTION

The technical solution of the present invention provides the new use of chlorogenic acid.

The use of chlorogenic acid or coumaroylquinic acid in the preparation of drugs for treatment of squamous cell carcinoma.

Wherein, said drug is a preparation obtained by using an effective amount of chlorogenic acid or coumaroylquinic acid as the active component, with the addition of pharmaceutically acceptable excipients or auxiliary ingredients.

Wherein, said pharmaceutical preparation contains 1-3000 mg chlorogenic acid/unit or 1-3000 mg coumaroylquinic acid/unit.

Wherein, the dosage of chlorogenic acid or coumaroylquinic acid in said pharmaceutical preparation is 1-100 mg/kg.

Wherein, said medicament is an oral preparation or an injection.

Wherein, said squamous cell carcinoma includes lung squamous cell carcinoma, head and neck squamous cell carcinoma, skin squamous cell carcinoma, oral squamous cell carcinoma, esophageal squamous cell carcinoma, cervical squamous cell carcinoma, and vaginal squamous cell carcinoma.

The present invention further provides a pharmaceutical composition, that contains chlorogenic acid and coumaroylquinic acid.

Further, the mass ratio of chlorogenic acid to coumaroylquinic acid is 100:0.01-10; Preferably, the mass ratio of chlorogenic acid to coumaroylquinic acid is 100:0.01-1; Preferably, the mass ratio of chlorogenic acid to coumaroylquinic acid is 100:0.01-0.1; More preferably, the mass ratio of chlorogenic acid to coumaroylquinic acid is 100:0.1.

The present invention provides a drug for treatment of squamous cell carcinoma, that is a commonly used pharmaceutical preparation obtained by using chlorogenic acid and coumaroylquinic acid as the active components, with the addition of pharmaceutically acceptable excipients.

Preferably, said preparation is an oral or injectable preparation.

The present invention provides the use of the pharmaceutical composition mentioned above in the preparation of drugs for treatment of squamous cell carcinoma.

Wherein, said squamous cell carcinoma includes lung squamous cell carcinoma, head and neck squamous cell carcinoma, skin squamous cell carcinoma, oral squamous cell carcinoma, esophageal squamous cell carcinoma, cervical squamous cell carcinoma, and vaginal squamous cell carcinoma.

Chlorogenic acid and coumaroylquinic acid of the present invention can be used alone to effectively treat squamous cell carcinoma, and the combination of them can also effectively treat squamous cell carcinoma. Under a certain ratio, both of them can also exert a synergistic effect, and thus the application prospect is excellent.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
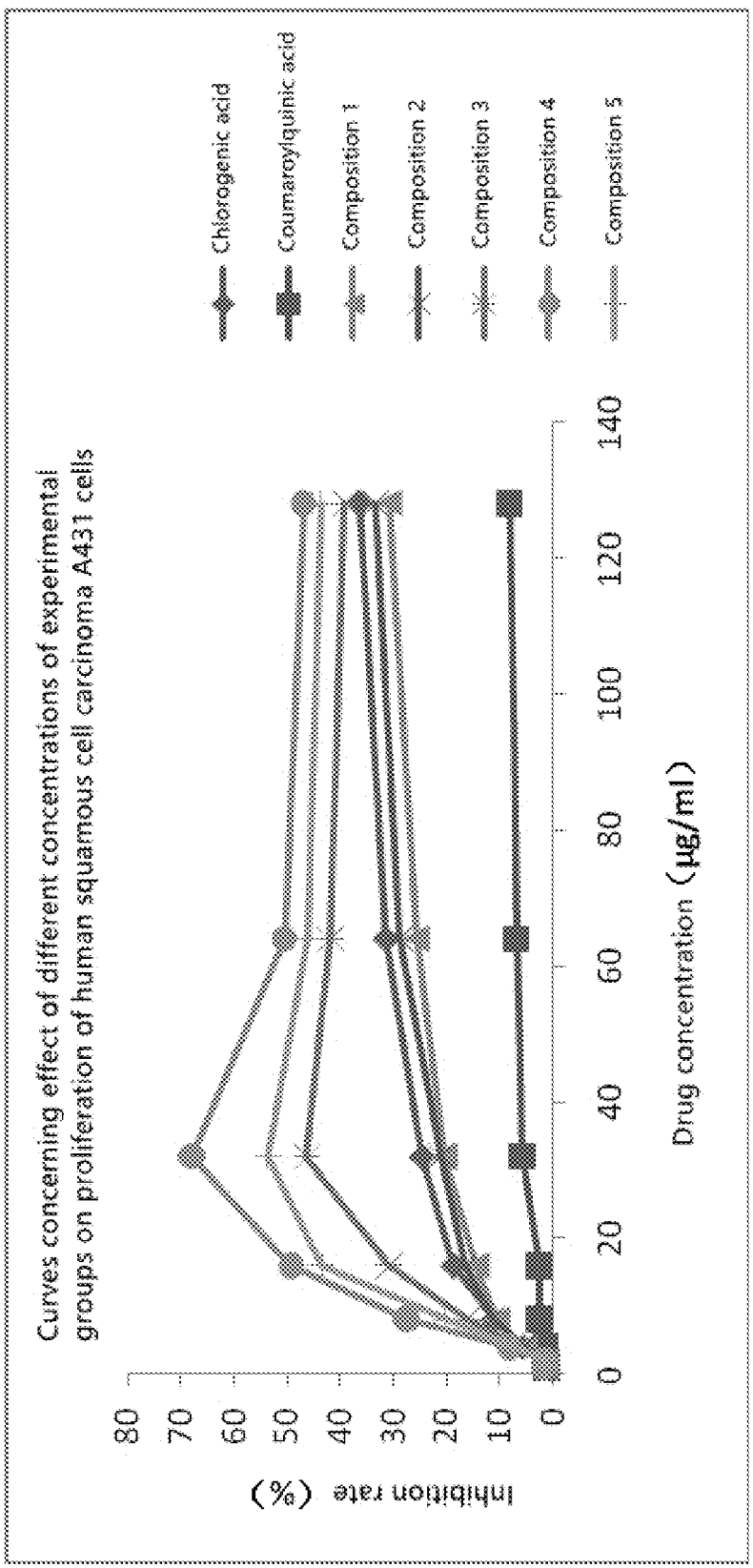
FIG. 1. The effect curves of each experimental group at different concentrations against the proliferation of human skin squamous cell carcinoma A431 cells.
Figure 2:
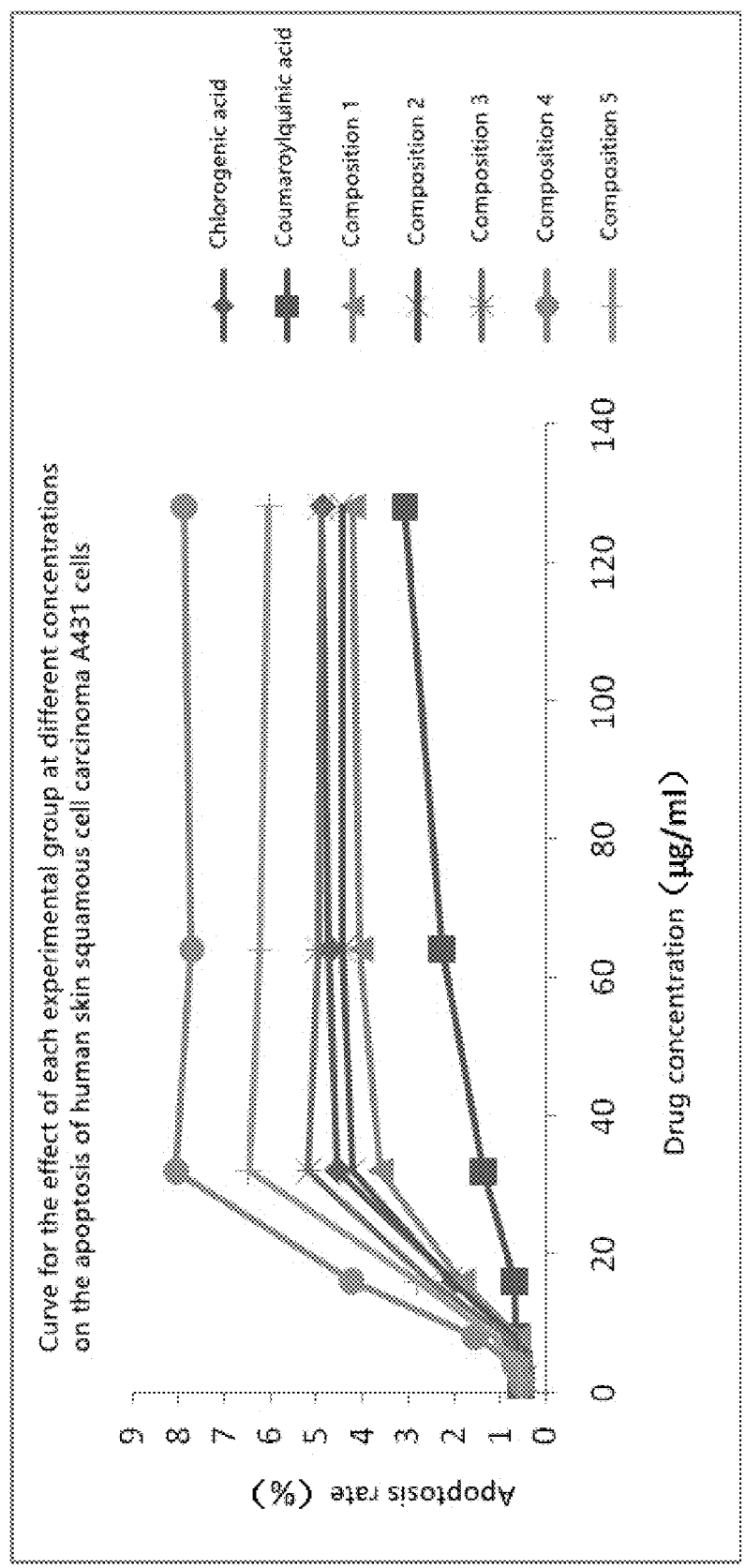
FIG. 2. The effect of each experimental group at different concentrations on the apoptosis of human skin squamous cell carcinoma A431 cells.
Figure 3:
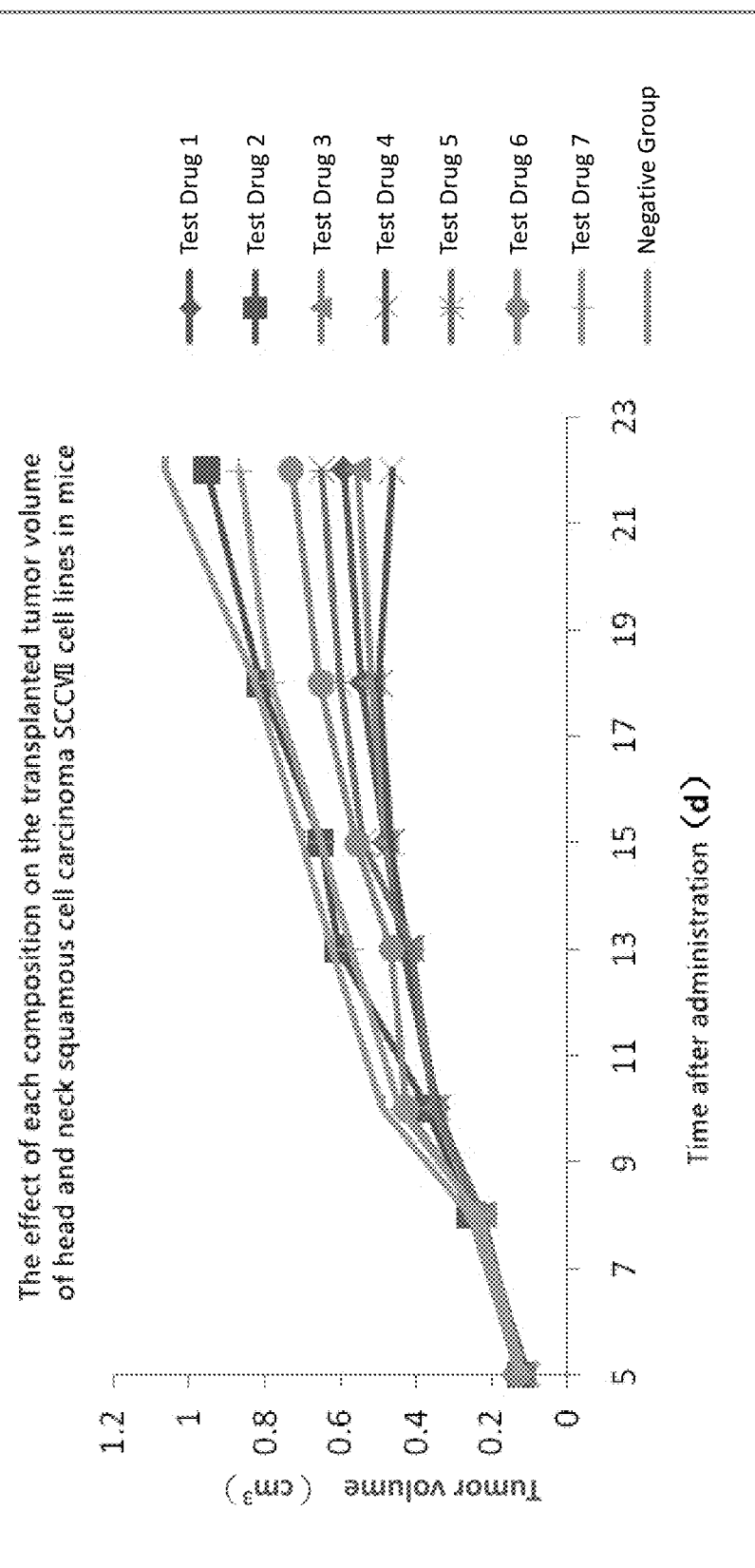
FIG. 3. The effect of each composition on the transplanted tumor volume of head and neck squamous cell carcinoma SCCVII cell lines in mice.
Figure 4:
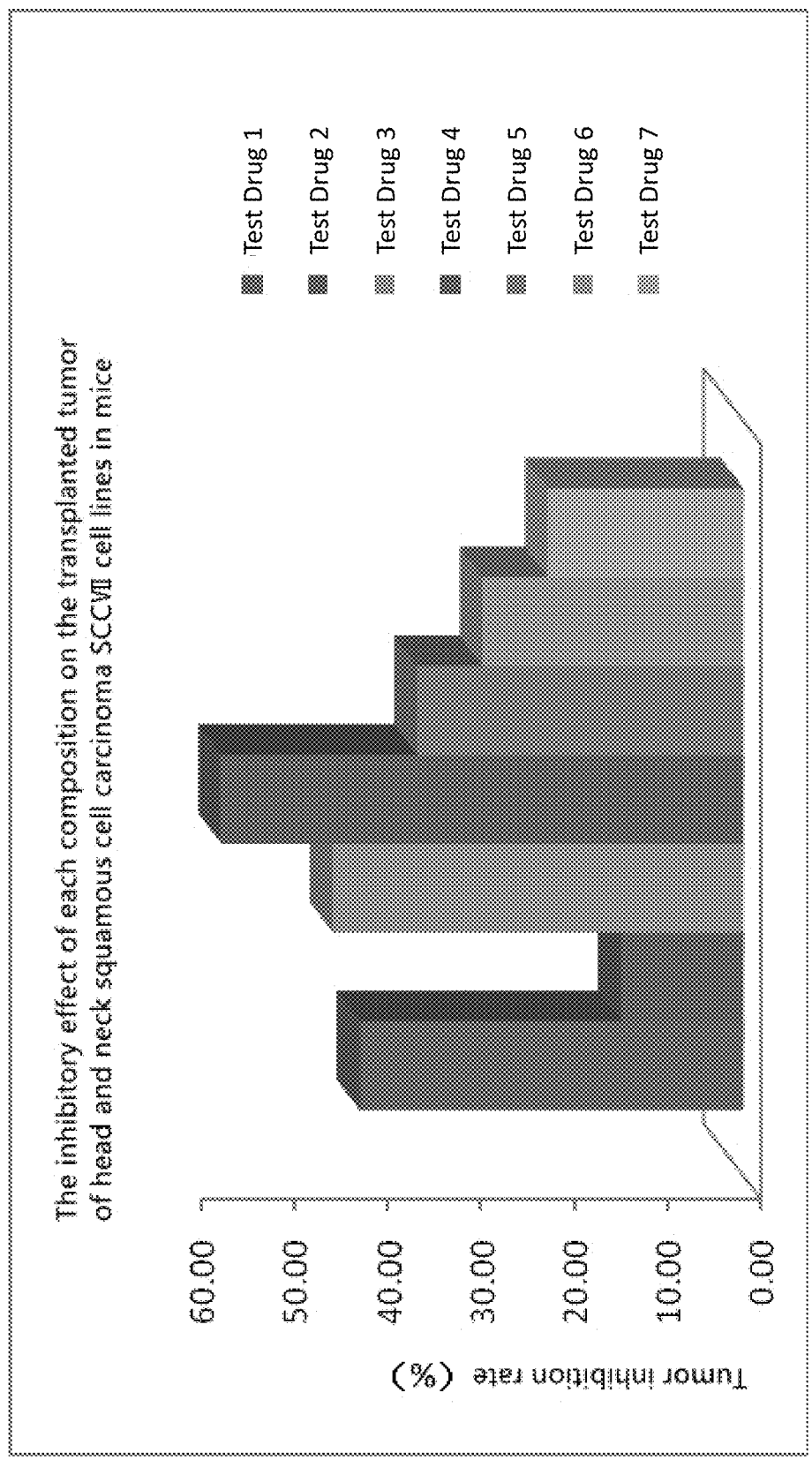
FIG. 4. The inhibitory effect of each composition on the transplanted tumor of head and neck squamous cell carcinoma SCCVII cell lines in mice.

The starting materials and equipment used in the specific examples of the present invention are all known products and can be obtained by purchasing commercially available products.

Example 1 the Formula for Oral Preparation of the Pharmaceutical Composition According to the Present Invention 1. Formula 1

Chlorogenic acid 1000 g, coumaroylquinic acid 1 g.

Preparative method: chlorogenic acid and coumaroylquinic acid were aseptically weighed according to the formula, mixed thoroughly, and aseptically subpacked as powders.

2. Formula 2

Chlorogenic acid 1000 g, coumaroylquinic acid 5 g, bulking agent 500 g, binding agent 5 g.

Preparative method: chlorogenic acid, coumaroylquinic acid, bulking agent, and binding agent were weighed according to the formula, granulated, sieved, and subpacked as granules.

3. Formula 3

Chlorogenic acid 1000 g, coumaroylquinic acid 1 g, bulking agent 500 g, binding agent 5 g, and lubricant 3 g.

Preparative method: chlorogenic acid, coumaroylquinic acid, bulking agent, and binding agent were weighed according to the formula, granulated, sieved, and then lubricant was added, followed by pressing, to obtain tablets.

Above bulking agents were one or more of mannitol, lactose, starch, microcrystalline cellulose, and dextrin; the binding agents were sodium carboxymethylcellulose and PVP; the lubricants were magnesium stearate, talcum powder, and micro silica gel.

Example 2 the Formula for Injection of the Pharmaceutical Composition According to the Present Invention 1. Formula 1

Chlorogenic acid 1000 g, coumaroylquinic acid 1 g.

Preparative method (1): chlorogenic acid and coumaroylquinic acid were aseptically weighed according to the formula, mixed thoroughly, and aseptically subpacked as powder injection.

Preparative method (2): chlorogenic acid and coumaroylquinic acid were weighed according to the formula, dissolved in water for injection, filtered, sterilized, and freeze-dried to obtain freeze-dried powder injection.

2. Formula 2

Chlorogenic acid 1000 g, coumaroylquinic acid 1 g, stent agent 2667 g, and antioxidant 67 g.

Preparative method: chlorogenic acid, coumaroylquinic acid, stent agent, and antioxidant were weighed according to the formula, dissolved in water for injection, filtered, sterilized, and freeze-dried to obtain freeze-dried powder injection.

Said stent agents were mannitol, lactose and glucose; the antioxidants were sodium bisulfite, vitamin, glutathione, and folic acid.

In the following, the beneficial effect of the present invention was ellucidated by experimental examples:

Experimental Example 1 In Vitro Investigation on the Inhibitory Effect of Chlorogenic Acid and the Composition Thereof on Squamous Cell Tumor 1 Materials 1.1 Cell tissue Human skin squamous cell carcinoma A431 cell lines were purchased from Wuhan Procell Life Science&Technology Co., Ltd.

1.2 Drugs Chlorogenic acid, coumaroylquinic acid, composition 1 of chlorogenic acid and coumaroylquinic acid (100:10), composition 2 of chlorogenic acid and coumaroylquinic acid (100:5), composition 3 of chlorogenic acid and coumaroylquinic acid (100:1), composition 4 of chlorogenic acid and coumaroylquinic acid (100:0.1), composition 5 of chlorogenic acid and coumaroylquinic acid (100:0.01); provided by Sichuan Jiuzhang Biological Science and Biotechnology Co., Ltd.

1.3 Reagents Dimethylsulfoxide (DMSO), methylthiazolyl tetrazolium (MTT), IMDM culture medium and fetal bovine serum, propidium iodide (PI), provided by Sigma.

2 Method 2.1 Cell Culture

A431 cell lines were seeded in IMDM medium, containing 10% fetal bovine serum, 100 $U \cdot ml^{-1}$ penicillin, and 100 $\mu g \cdot ml^{-1}$ streptomycin, and then cultured in 37° C., 5% $CO_2$ incubator. Cells were passaged one generation at 48-72 h, and the cells in the logarithmic growth phase were collected for the experiment.

2.2 Experiment on the Inhibition of Cell Proliferation (MTT Method)

The cells in logarithmic growth phase were inoculated on 96 well plate and further cultured for 24 hours, then divided into experimental groups and blank control group. The experimental groups were added with 100 µl IMDM culture medium of chlorogenic acid group, coumaroylquinic acid group, composition group 1, composition group 2, composition group 3, composition group 4, and composition group 5, respectively, and the final concentration of each test sample was 128 µg/ml, 64 µg/ml, 32 µg/ml, 16 µg/ml, 8 µg/ml, 4 µg/ml, 2 µg/ml, and 1 g/ml. The blank control group was added with the same volume of IMDM culture medium without test substance. Six multiple wells were set for each concentration. After 72 hours, the newly prepared MTT solution was added. After further culturing for 4 h, DMSO solution was added and shook, so that the crystals were fully dissolved. The absorbance value (A570 nm) of each well was measured on the microplate reader. The average value of six wells was obtained, and the cell inhibiting rate was calculated according to the formula: the inhibition rate=(1−the average value of A570 nm in the experimental group/the average value of A570 nm in the control group)×100%.

2.3 Detecting Apoptosis by Flow Cytometry

The cells of each group treated with different concentrations of test substance for 72 h were collected and made into single cell suspension. The living cells were labeled with Annexin V-FITC and PI. After mixing, the cells were incubated in dark for 15 min at room temperature, and then 1× binding buffer was added and mixed, before the apoptotic cells were detected by flow cytometry and analyzed by Multicyc AV software.

2.4 Statistical Analysis

Results were analyzed by SPSS 19.0 statistical software.

3 Experimental Results 3.1 Effect of each experimental group at different concentrations on proliferation of human skin squamous cell carcinoma A431 cells

TABLE 1

Effect of each experimental group at different concentrations on proliferation of human skin squamous cell carcinoma A431 cells ($\bar{x} \pm s$).

| | Concentration (μg/ml) | 1 | 2 | 4 | 8 | 16 |
|---|---|---|---|---|---|---|
| The inhibition rate of each experimental group (%) | Chlorogenic acid | 1.12 ± 0.47 | 1.38 ± 0.53 | 5.63 ± 2.29 | 11.02 ± 4.71 | 18.64 ± 4.82 |
| | Coumaroylquinic acid | 1.24 ± 0.81 | 1.28 ± 0.69 | 1.33 ± 0.42 | 2.41 ± 0.58 | 2.62 ± 0.86 |
| | Composition 1 | 1.11 ± 0.29 | 1.31 ± 0.74 | 5.33 ± 1.25 | 10.52 ± 2.89 | 14.38 ± 3.53 |
| | Composition 2 | 1.04 ± 0.26 | 1.22 ± 0.47 | 5.47 ± 0.83 | 11.38 ± 3.33 | 16.42 ± 5.35 |
| | Composition 3 | 1.25 ± 0.39 | 1.25 ± 0.71 | 6.04 ± 1.38 | 16.25 ± 5.37 | 30.84 ± 8.09* |
| | Composition 4 | 1.43 ± 0.53 | 1.46 ± 0.61 | 8.24 ± 1.52 | 27.61 ± 5.62* | 49.34 ± 10.85* |
| | Composition 5 | 1.26 ± 0.34 | 1.25 ± 0.77 | 7.25 ± 3.11 | 20.23 ± 2.18 | 43.52 ± 12.86* |

| | Concentration (μg/ml) | 32 | 64 | 128 |
|---|---|---|---|---|
| The inhibition rate of each experimental group (%) | Chlorogenic acid | 24.52 ± 9.69 | 31.37 ± 7.35* | 36.32 ± 10.84* |
| | Coumaroylquinic acid | 5.77 ± 0.92 | 6.83 ± 1.02 | 8.11 ± 0.63 |
| | Composition 1 | 20.44 ± 6.47 | 25.72 ± 9.09 | 30.81 ± 12.74* |
| | Composition 2 | 21.13 ± 4.26 | 28.89 ± 5.15* | 33.46 ± 7.97* |
| | Composition 3 | 46.38 ± 12.52* | 42.03 ± 9.11* | 39.22 ± 11.41* |
| | Composition 4 | 68.06 ± 13.28* | 50.52 ± 15.46* | 46 93 ± 8.59* |
| | Composition 5 | 53.69 ± 16.47* | 46.34 ± 11.09* | 43.57 ± 12.86* |

Note:
*indicates a significant difference compared with the blank group ($p < 0.05$)*

The results showed that: (1) in all test drug groups, except that the inhibitory effect of coumaroylquinic acid on human skin squamous cell carcinoma A431 was not obvious, the other test drug groups had significant inhibitory effect on human skin squamous cell carcinoma A431, wherein composition 4>composition 5>composition 3>chlorogenic acid>composition 2>composition 1>coumaroylquinic acid; (2) the inhibitory effect of chlorogenic acid group, composition 1 group and composition 2 group on human skin squamous cell carcinoma A431 presented a dose-dependent relationship, and for the concentration ranging from 16 μg/ml to 128 μg/ml, at the same concentration, the inhibitory effect of compositions 1 and 2 was slightly lower than that of chlorogenic acid single compound, indicating that the inhibitory effect of chlorogenic acid on human skin squamous cell carcinoma A431 was better than that of compositions 1 and 2; (3) the inhibitory effect of composition 3 group, composition 4 group and composition 5 group at the concentration range of 1-128 μg/ml on human skin squamous cell carcinoma A431 was first increased and then decreased, and the effect at the concentration of 32-64 μg/ml was all the best, in which the inhibition effect of composition 4 was the best.

3.2

TABLE 2

Effect of each experimental group at different concentrations on apoptosis of human skin squamous cell carcinoma A431 cells ($\bar{x} \pm s$).

| | Drug concentration (μg/ml) | 1 | 2 | 4 | 8 | 16 | 32 | 64 | 128 |
|---|---|---|---|---|---|---|---|---|---|
| Apoptosis rate of each experimental group (%) | Chlorogenic acid | 0.57 ± 0.04 | 0.57 ± 0.05 | 0.61 ± 0.06 | 0.71 ± 0.11 | 1.99 ± 0.57 | 4.56 ± 1.08* | 4.73 ± 1.22* | 4.87 ± 0.74* |
| | Coumaroylquinic acid | 0.53 ± 0.03 | 0.55 ± 0.05 | 0.56 ± 0.04 | 0.64 ± 0.13 | 0.69 ± 0.41 | 1.37 ± 0.36 | 2.26 ± 0.69 | 3.07 ± 1.23 |
| | Composition 1 | 0.55 ± 0.05 | 0.54 ± 0.08 | 0.59 ± 0.11 | 0.62 ± 0.08 | 1.84 ± 0.62 | 3.62 ± 1.33 | 4.06 ± 1.17* | 4.23 ± 0.49* |
| | Composition 2 | 0.58 ± 0.06 | 0.56 ± 0.07 | 0.56 ± 0.08 | 0.69 ± 0.12 | 2.09 ± 0.85 | 4.21 ± 0.94* | 4.42 ± 0.77* | 4.45 ± 0.86* |
| | Composition 3 | 0.54 ± 0.06 | 0.51 ± 0.02 | 0.58 ± 0.11 | 0.82 ± 0.09 | 2.52 ± 0.52 | 5.17 ± 0.85* | 4.97 ± 1.03* | 4.88 ± 1.81* |

TABLE 2-continued

Effect of each experimental group at different concentrations on apoptosis of human skin squamous cell carcinoma A431 cells ($\bar{x} \pm s$).

| Drug concentration (µg/ml) | 1 | 2 | 4 | 8 | 16 | 32 | 64 | 128 |
|---|---|---|---|---|---|---|---|---|
| Composition 4 | 0.52 ± 0.07 | 0.55 ± 0.03 | 0.68 ± 0.05 | 1.56 ± 0.38 | 4.23 ± 1.05* | 8.06 ± 2.12* | 7.72 ± 0.96* | 7.89 ± 1.34* |
| Composition 5 | 0.56 ± 0.04 | 0.54 ± 0.11 | 0.63 ± 0.03 | 1.12 ± 0.13 | 2.79 ± 0.78 | 6.47 ± 1.43* | 6.22 ± 1.27* | 6.04 ± 0.58* |
| Blank group | | | | | 0.57 ± 0.02 | | | |

Note:
*indicates a significant difference compared with the blank group ($p < 0.05$)*

4 Summary

The experimental results showed that: (1) the killing effect of each drug group on human skin squamous cell carcinoma A431 was weak, and the apoptosis rate was low. Among the experimental groups, the effect of composition 4 on the apoptosis of A431 cells was more significant, the second is composition 5 and composition 3, and the third is chlorogenic acid, followed by composition 2 and composition 1. In the trend of affecting A431 cell apoptosis, except that chlorogenic acid and compositions 2 and 1 presented a dose-dependent relationship, the other groups all increased first and then decreased, and the effect at the concentration range of 32-64 µg/ml was more significant.

Experimental Example 2 Investigation of Chlorogenic Acid and the Composition Thereof Inhibiting Squamous Cell Tumor 1 Materials 1.1 Test Drugs
Test drug 1: Chlorogenic acid
Test drug 2: Coumaroylquinic acid
Test drug 3: composition of chlorogenic acid and coumaroylquinic acid (100:0.01)
Test drug 4: composition of chlorogenic acid and coumaroylquinic acid (100:0.1)
Test drug 5: composition of chlorogenic acid and coumaroylquinic acid (100:1)
Test drug 6: composition of chlorogenic acid and coumaroylquinic acid (100:5)
Test drug 7: composition of chlorogenic acid and coumaroylquinic acid (100:10)
1.2 Animals C3H/HeJ mice, female, 6-8 weeks; purchased from Institute of Experimental Animals, Chinese Academy of Medical Sciences.
1.3 Cell tissue Mouse head and neck squamous cell carcinoma (abbreviated as squamous cancer) SCC VII cell lines, purchased from Johns Hopkins University, USA.
1.4 Drugs chlorogenic acid, coumaroylquinic acid; provided by Sichuan Jiuzhang Biological Science and Biotechnology Co., Ltd.

2 Methods 2.1 Tumor Cell Culture

Head and neck squamous cell carcinoma SCCVII cell lines were cultured in 1640 medium containing 12.5% calf serum at 37° C. and 5% $CO_2$. When the cells grew vigorously, they were digested with 0.25% trypsin, washed with phosphate buffer, and prepared as cell suspension at $3 \times 10^6$ cells/ml for use.

2.2 In Vivo Experiment 0.1 ml cell suspension was subcutaneously injected into the armpit of the left forelimb of mice. They were randomly divided into groups, 10 mice for one group, including test drug group 1, test drug group 2, test drug group 3, test drug group 4, test drug group 5, test drug group 6, test drug group 7, and negative group (N.S.), respectively. The drug was given on the second day after inoculation. The test drug group was intraperitoneally injected at a dose of 30 mg·kg$^{-1}$, once a day, and the administration volume was 1.0 ml; in the negative group, the same volume of normal saline was intraperitoneally injected, once a day.

The tumor volume (v=0.52×the long diameter of transplanted tumor L×the shortest diameter of transplanted tumor $W^2$) was measured on the 5th day after inoculation, and the mice were weighed every three days. When the tumor volume of the negative group was about 1.0 cm$^3$, the experiment was stopped, and the mice were killed by cervical dislocation and weighed. The tumor was stripped, and the tumor inhibition rate was calculated: the tumor inhibition rate %=[1−(the average tumor weight of the test drug group/the average tumor weight of the negative group)]×100%.

3 Results

TABLE 3

Tumor volume of mice (with head and neck squamous cell carcinoma SCCVII cell lines) in the test drug group and the blank group ($\bar{x} \pm s$, cm$^3$).

| Time after inoculation | 5 d | 8 d | 10 d | 13 d | 15 d | 18 d | 22 d |
|---|---|---|---|---|---|---|---|
| Test drug group 1 | 0.124 ± 0.083 | 0.222 ± 0.079 | 0.347 ± 0.102 | 0.436 ± 0.172* | 0.483 ± 0.136* | 0.545 ± 0.224* | 0.593 ± 0.125* |
| Test drug group 2 | 0.124 ± 0.047 | 0.258 ± 0.121 | 0.369 ± 0.114 | 0.604 ± 0.225* | 0.653 ± 0.111* | 0.811 ± 0.108* | 0.954 ± 0.203* |
| Test drag group 3 | 0.118 ± 0.035 | 0.223 ± 0.075 | 0.354 ± 0.068 | 0.417 ± 0.148* | 0.481 ± 0.139* | 0.518 ± 0.172* | 0.554 ± 0.089* |
| Test drug group 4 | 0.106 ± 0.044 | 0.236 ± 0.038 | 0.343 ± 0.093 | 0.426 ± 0.116* | 0.468 ± 0.084* | 0.498 ± 0.156* | 0.464 ± 0.117* |
| Test drug group 5 | 0.112 ± 0.071 | 0.229 ± 0.113 | 0.352 ± 0.099 | 0.411 ± 0.095* | 0.541 ± 0.158 | 0.602 ± 0.199* | 0.649 ± 0.212* |
| Test drug group 6 | 0.131 ± 0.056 | 0.240 ± 0.061 | 0.427 ± 0.137 | 0.465 ± 0.067* | 0.557 ± 0.174* | 0.654 ± 0.147* | 0.731 ± 0.174* |
| Test drug group 7 | 0.116 ± 0.062 | 0.231 ± 0.092 | 0.444 ± 0.084 | 0.572 ± 0.137* | 0.651 ± 0.121* | 0.782 ± 0.252* | 0.868 ± 0.193* |
| Negative group | 0.127 ± 0.039 | 0.257 ± 0.088 | 0.488 ± 0.177 | 0.621 ± 0.214 | 0.702 ± 0.263 | 0.827 ± 0.149 | 1.062 ± 0.228 |

Compared with negative group,
*$p < 0.05$

TABLE 4

Effects of each composition on the tumor volume in mice transplanted with head and neck squamous cell carcinoma SCCVII cell lines (x ± s, cm³)

| Groups | Dose (mg · kg⁻¹) | Tumor weight (g) | Tumor inhibition rate (%) |
|---|---|---|---|
| Chlorogenic acid | 30 | 1.43 ± 0.074 * | 41.15 |
| Coumaroylquinic acid | 30 | 2.11 ± 0.129 | 13.17 |
| Test drug group 3 | 30 | 1.36 ± 0.054 * | 44.03 |
| Test drug group 4 | 30 | 1.07 ± 0.097 * | 55.97 |
| Test drug group 5 | 30 | 1.58 ± 0.096 * | 34.98 |
| Test drug group 6 | 30 | 1.75 ± 1.11 * | 27.98 |
| Test drug group 7 | 30 | 1.92 ± 0.93 * | 20.99 |
| Negative group | N.S | 2.43 ± 0.89 | — |

Compared with negative group,
* $p < 0.05$

4 Summary

The experimental results showed that chlorogenic acid and compositions 3-5 of chlorogenic acid and coumaroylquinic acid had significant differences compared with the negative group, indicating that they had inhibitory effects on the tumors in mice transplanted with head and neck squamous cell carcinoma SCCVII cell lines, wherein composition 4 and composition 3 had better inhibitory effects, followed by chlorogenic acid and composition 5. The inhibitory effect of coumaroylquinic acid was not obvious, indicating that coumaroylquinic acid itself was not sensitive to transplanted tumors of the head and neck squamous cell carcinoma SCCVII cell lines in mice; in addition, compositions 6 and 7 did not show significant difference compared with the negative group, indicating that the composition of chlorogenic acid and coumaroylquinic acid did not necessarily have a synergistic effect on the transplated tumor of head and neck squamous cell carcinoma SCCVII cell lines in mice, but only in a certain ratio, the synergistic effect could be achieved.

Chlorogenic acid and coumaroylquinic acid of the present invention had clear therapeutic effects in treating squamous cell carcinoma, especially skin squamous cell carcinoma. The chlorogenic acid composition of the present invention, which contained chlorogenic acid and coumaroylquinic acid, could effectively treat squamous cell carcinoma, and in a certain ratio, chlorogenic acid and coumaroylquinic acid could be used in combination, and have synergistic effect.

The invention claimed is:

1. A method of treating squamous cell carcinoma, comprising administering an effective amount of a composition comprising chlorogenic acid and a coumaroylquinic acid to a subject in need thereof, wherein the mass ratio of chlorogenic acid to coumaroylquinic acid is 100:0.01-1.

2. The method according to claim 1, wherein the composition further comprises pharmaceutically acceptable excipients or auxiliary ingredients.

3. The method according to claim 2, wherein the composition contains 1-3000 mg chlorogenic acid/unit.

4. The method according to claim 3, wherein a dosage of chlorogenic acid is 1-100 mg/kg.

5. The method according to claim 3, wherein the composition is formulated for injection or oral administration.

6. The method according to claim 1, wherein the squamous cell carcinoma is selected from lung squamous cell carcinoma, head and neck squamous cell carcinoma, skin squamous cell carcinoma, oral squamous cell carcinoma, esophageal squamous cell carcinoma, cervical squamous cell carcinoma, and vaginal squamous cell carcinoma.

* * * * *